(12) United States Patent
Montag et al.

(10) Patent No.: US 10,687,761 B2
(45) Date of Patent: Jun. 23, 2020

(54) CATHETER FRAME PIECES USED AS LARGE SINGLE AXIS SENSORS

(71) Applicant: BIOSENSE WEBSTER (ISRAEL) LTD., Yokneam (IL)

(72) Inventors: Avram Dan Montag, Haifa (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1001 days.

(21) Appl. No.: 14/757,678

(22) Filed: Dec. 23, 2015

(65) Prior Publication Data

US 2017/0181706 A1    Jun. 29, 2017

(51) Int. Cl.
    *A61B 5/05*      (2006.01)
    *A61B 5/00*      (2006.01)
    (Continued)

(52) U.S. Cl.
CPC .......... *A61B 5/6856* (2013.01); *A61B 5/0422* (2013.01); *A61B 5/05* (2013.01); *A61B 5/062* (2013.01); *A61B 5/065* (2013.01); *A61B 5/6852* (2013.01); *A61B 18/1492* (2013.01); *A61N 1/056* (2013.01); *A61B 5/042* (2013.01); *A61B 5/0402* (2013.01); *A61B 5/6858* (2013.01); *A61B 2018/00011* (2013.01); *A61B 2018/00267* (2013.01); *A61B 2018/00351* (2013.01); *A61B 2018/00357* (2013.01); *A61B 2018/00577* (2013.01); *A61B 2018/00839* (2013.01); *A61B 2018/1407* (2013.01); *A61B 2034/2051* (2016.02)

(58) Field of Classification Search
CPC ... A61B 5/6856; A61B 5/6852; A61B 5/0422; A61B 5/065; A61B 5/062; A61B 18/1492; A61B 5/05; A61B 2034/2051; A61B 2018/1407; A61B 5/6858; A61B 2018/00267; A61B 2018/00351; A61B 5/04; A61N 1/056
See application file for complete search history.

(56) References Cited

U.S. PATENT DOCUMENTS

| | | | |
|---|---|---|---|
| 5,443,489 | A | 8/1995 | Ben-Haim |
| 5,480,422 | A | 1/1996 | Ben-Haim |

(Continued)

FOREIGN PATENT DOCUMENTS

| | | |
|---|---|---|
| EP | 1 529 548 A2 | 5/2005 |
| EP | 2 875 779 A1 | 5/2015 |

(Continued)

OTHER PUBLICATIONS

European Search Report dated May 24, 2017 from corresponding European Patent Application No. 16206174.1.

*Primary Examiner* — Rajeev P Siripurapu

(57) ABSTRACT

Catheterization of the heart is carried out using a framework formed by a plurality of electrically conducting wire loops. The wire loops are modeled as polygons, each subdivided into a plurality of triangles. The wire loops are exposed to magnetic fluxes at respective frequencies, and signals read from the loops. Theoretical magnetic fluxes in the polygons are computed as sums of theoretical magnetic fluxes in the triangles thereof, The location and orientation of the framework in the heart is determined by relating the computed theoretical magnetic fluxes to the signals.

12 Claims, 8 Drawing Sheets

(51) Int. Cl.
  *A61N 1/05* (2006.01)
  *A61B 5/042* (2006.01)
  *A61B 5/06* (2006.01)
  *A61B 18/14* (2006.01)
  *A61B 18/00* (2006.01)
  *A61B 34/20* (2016.01)
  *A61B 5/0402* (2006.01)

(56) References Cited

U.S. PATENT DOCUMENTS

| | | |
|---|---|---|
| 5,546,951 A | 8/1996 | Ben-Haim |
| 5,558,091 A | 9/1996 | Acker et al. |
| 5,568,809 A | 10/1996 | Ben-Haim |
| 5,772,590 A | 6/1998 | Webster, Jr. |
| 6,226,542 B1 | 5/2001 | Reisfeld |
| 6,266,551 B1 | 7/2001 | Osadchy et al. |
| 6,301,496 B1 | 10/2001 | Reisfeld |
| 6,335,617 B1 | 1/2002 | Osadchy et al. |
| 6,370,411 B1 | 4/2002 | Osadchy et al. |
| 6,814,733 B2 | 11/2004 | Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,756,576 B2 | 7/2010 | Levin |
| 8,818,486 B2 * | 8/2014 | Montag ............... A61B 5/062 324/207.13 |
| 2015/0196216 A1 * | 7/2015 | Laughner ............ A61B 5/0422 600/374 |
| 2015/0208937 A1 * | 7/2015 | Bullinga ............. A61B 5/0408 600/424 |
| 2018/0042491 A1 * | 2/2018 | Smaill ................. A61B 5/0044 |

FOREIGN PATENT DOCUMENTS

| | | |
|---|---|---|
| WO | WO 95/02995 A1 | 2/1995 |
| WO | WO 97/24983 A2 | 7/1997 |
| WO | WO 98/29033 A1 | 7/1998 |
| WO | WO 2008/124222 A1 | 10/2008 |
| WO | WO 2015/106254 A1 | 7/2015 |

* cited by examiner

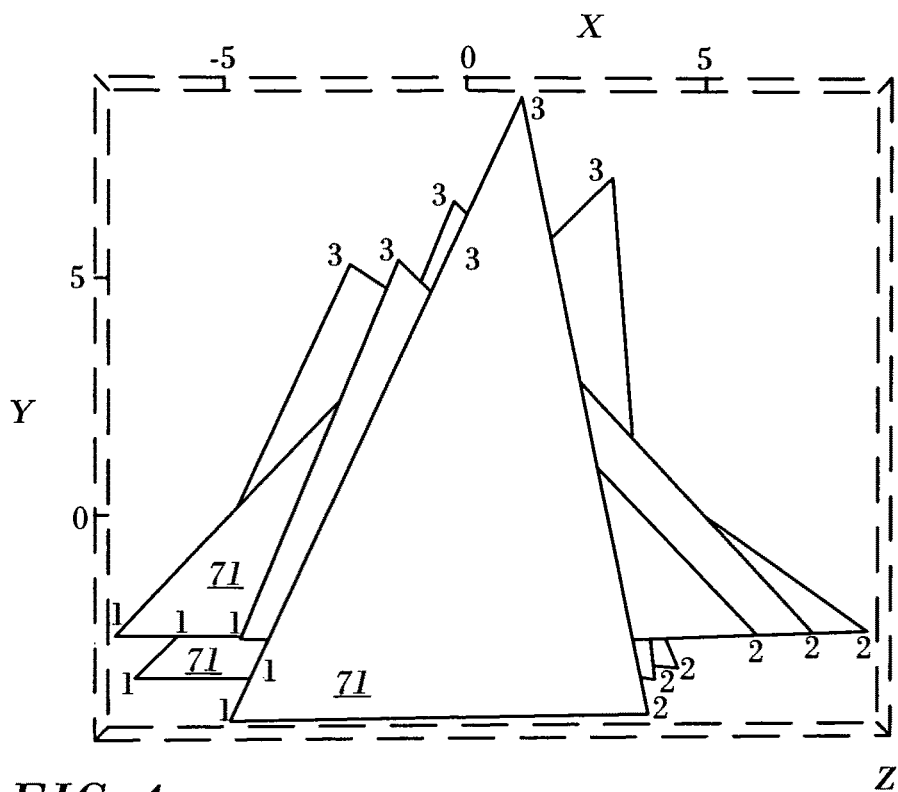
FIG. 4
FIG. 5
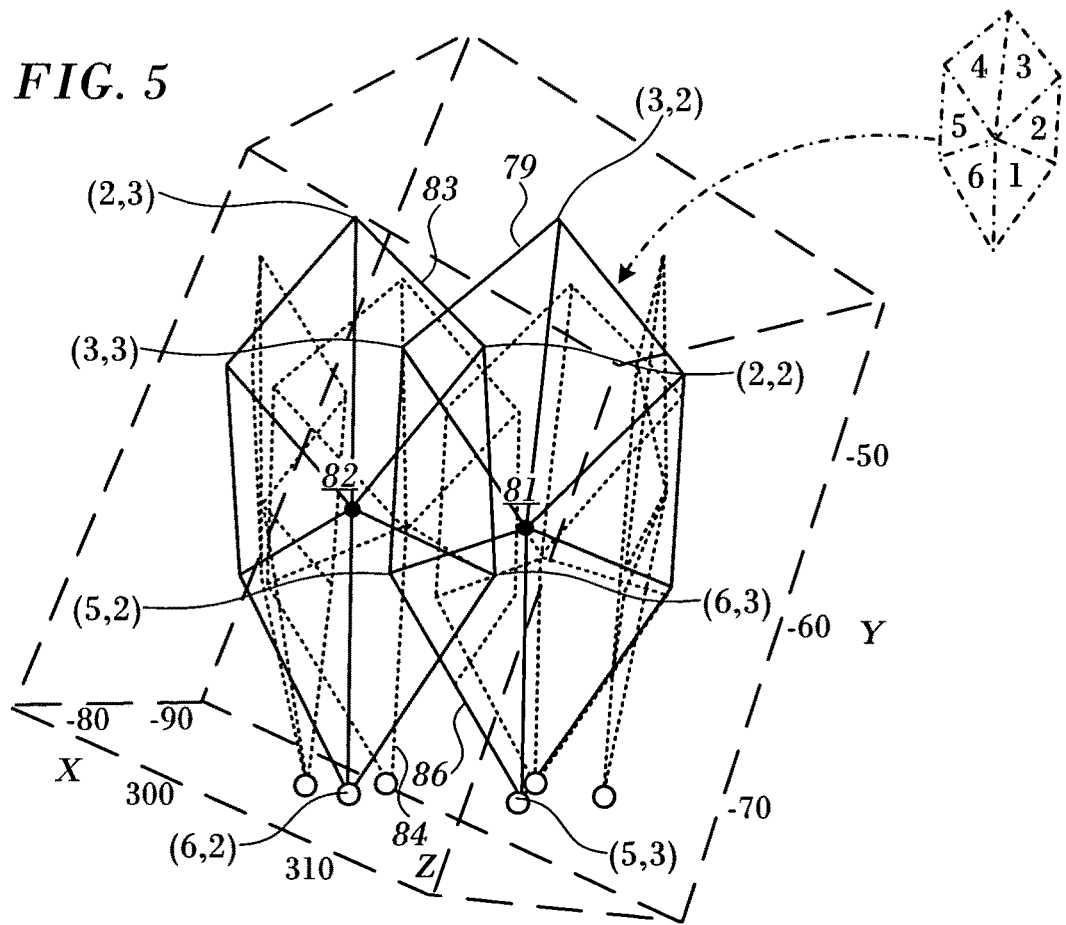

CATHETER FRAME PIECES USED AS LARGE SINGLE AXIS SENSORS

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to apparatus and processes for diagnostic and surgical purposes. More particularly, this invention relates to an intra-body probe having a sensor of electromagnetic fields.

2. Description of the Related Art

Electrophysiology catheters are commonly-used for mapping electrical activity in the heart. Various electrode designs are known for different purposes. In particular, catheters having basket-shaped electrode arrays are known and described, for example, in U.S. Pat. No. 5,772,590, the disclosure of which is incorporated herein by reference. Such catheters are typically introduced into a patient through a guiding sheath with the electrode array in a folded position within the sheath so that the electrode array does not damage the patient during introduction. Within the heart, the guiding sheath is removed and the electrode array is permitted to expand to be generally basket-shaped. Some basket catheters include an additional mechanism in the form of a wire or the like connected to an appropriate control hand to assist in the expansion and contraction of the electrode array.

Such catheters may incorporate magnetic location sensors as described, for example, in U.S. Pat. Nos. 5,558,091, 5,443,489, 5,480,422, 5,546,951, and 5,568,809, and International Publication Nos. WO 95/02995, WO 97/24983, and WO 98/29033, the disclosures of which are incorporated herein by reference. Such electromagnetic mapping sensors typically have a length of from about 3 mm to about 7 mm.

SUMMARY OF THE INVENTION

It is common for multi-electrode catheters to have a wire frame on which electrodes are mounted. Embodiments of the invention provide a framework comprising several loops of wire forming a cage-like structure. When the frame is subjected to an electromagnetic field, each of the loops functions as a single axis magnetic sensor. Moreover, by partitioning the loops into triangles bends in the structure can be reconstructed. A solution, accurate to about a millimeter, can be obtained for each loop's location. An overall solution for the position of the catheter can be derived from data obtained from the loops.

There is provided according to embodiments of the invention a probe adapted for insertion into a heart of a living subject. A framework disposed on the distal end is formed by a plurality of electrically conducting wire loops defining a chamber. The loops are independently connectable to a receiver. There may be six to seven wire loops.

According to an aspect of the apparatus, the wire loops form spirals about an axis.

According to one aspect of the apparatus, the wire loops are deformable for deployment through a catheter lumen.

According to a further aspect of the apparatus, one of the wire loops contacts at least another of the wire loops.

There is further provided according to embodiments of the invention a method which is carried out by inserting a probe into a heart of a living subject. A framework disposed on the distal end is formed by a plurality of electrically conducting wire loops defining a chamber. The loops are independently connectable to a receiver. The method is further carried out by modeling the wire loops as respective polygons, subdividing the polygons into a plurality of triangles, exposing the wire loops to magnetic fluxes at respective frequencies, reading signals from the wire loops responsively to the magnetic fluxes at the respective frequencies, computing the theoretical magnetic fluxes in the polygons as respective sums of theoretical magnetic fluxes in the triangles thereof, and determining a location and orientation of the framework by relating the computed theoretical magnetic fluxes to the signals.

According to an aspect of the method, the polygons are hexagons.

In one aspect of the method subdividing the polygons into a plurality of triangles includes identifying local coordinates of the triangles in a local coordinate system, and transforming the local coordinates of the triangles to coordinates of a magnetic position tracking system.

According to another aspect of the method, transforming the local coordinates is performed by optimizing a cost function.

According to a further aspect of the method, computing the theoretical magnetic fluxes is based on areas and centroids of the triangles.

According to yet another aspect of the method, modeling the wire loops also includes applying a first constraint, wherein segments of the triangles of adjacent polygons are required to intersect.

According to still another aspect of the method, modeling the wire loops also includes applying a second constraint, wherein a vertex of each triangle of one polygon coincides with a vertex of an adjacent triangle of the one polygon.

According to an additional aspect of the method, modeling the wire loops also includes applying a third constraint, wherein adjacent polygons contact one another at exactly two points.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIG. 4, which is a representation of the triangles in the model shown in FIG. 3 in accordance with an embodiment of the invention;

FIG. 5 is a model similar to FIG. 3 that illustrates the intersection of faces in accordance with an embodiment of the invention;

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.
Overview.

Figure 1:
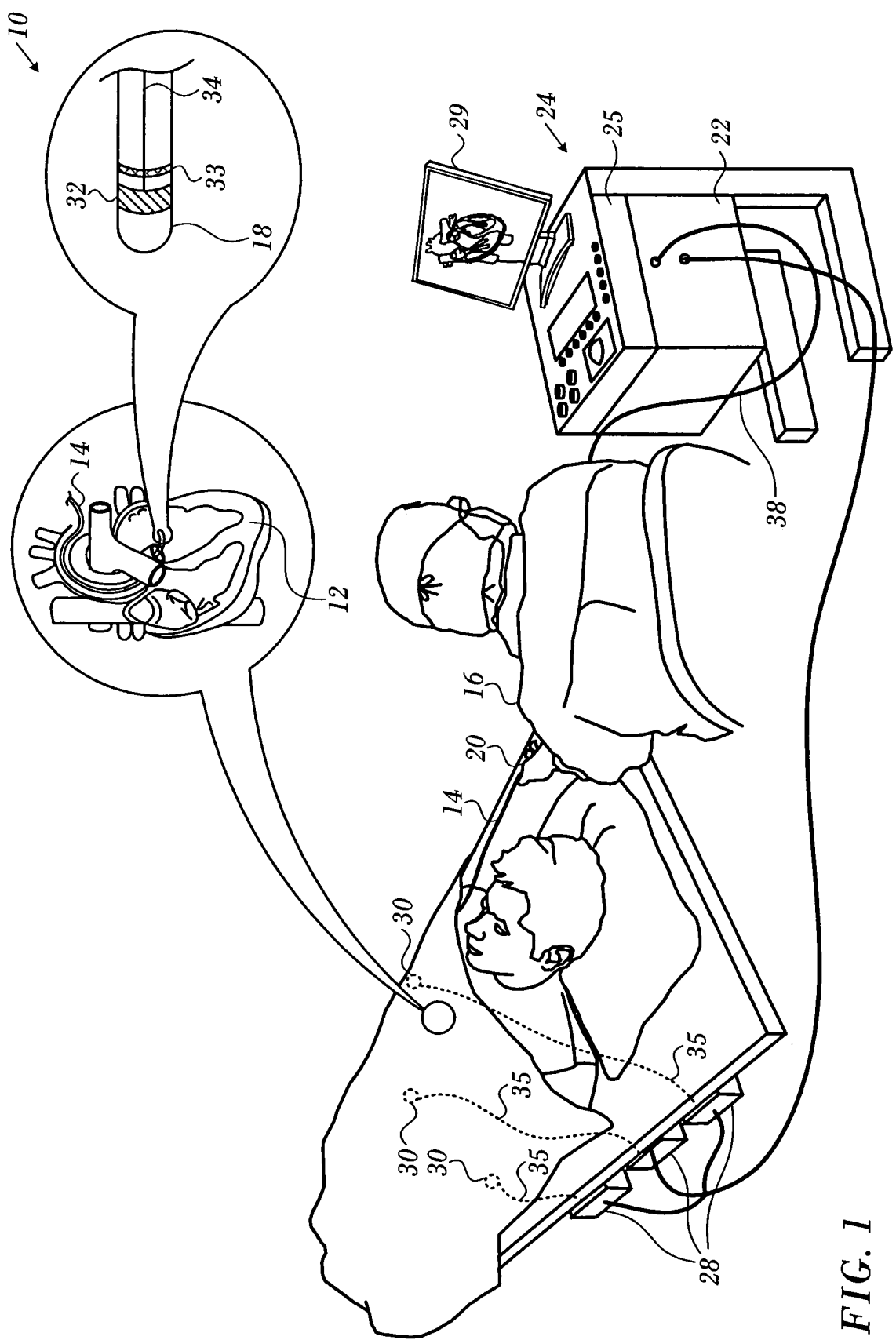
FIG. 1 is a pictorial illustration of a system for evaluating electrical activity in a heart of a living subject in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images that are described below.

Figure 2:
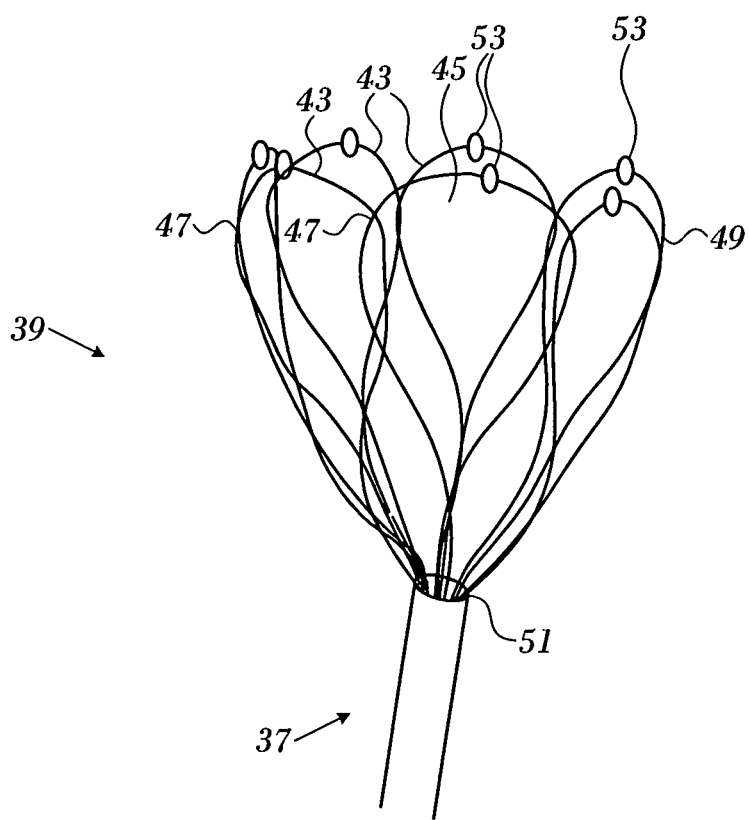
FIG. 2 is an elevation of a multi-electrode catheter in accordance with an embodiment of the invention.

Reference is now made to FIG. 2, which is an elevation of a multi-electrode catheter 37, in accordance with an embodiment of the invention. A framework 39 is deformable and deployable through a shaft 41. The framework 39 comprises several closed electrically conducting resilient wire loops 43, typically at least 6 or 7 loops, as shown in FIG. 2, defining a chamber 45. Each of the loops 43 functions independently as a single-axis magnetic location sensor when subjected to the magnetic field produced by field generating coils 28 (FIG. 1). The loops 43 are electrically insulated from one another. Adjacent loops 43 contact one another and intersect, e.g., at points 47, or be tangent, e.g., at point 49. As the framework 39 deforms, the springiness of the structure keeps the loops 43 in contact, and the points of contact can slide along the frame. A larger or smaller number of loops than shown in FIG. 2 may be provided on the framework 39, limited by mechanical requirements of size, flexibility and number of electrodes desired. Three to eight loops are practical. The loops 43 in a current embodiment have areas of about 300 mm$^2$ such that the area bounded by a loop is the same order of magnitude as the area of one of the magnetic sensor coils (number of turns times coil area) in conventional catheters, such as the Navistar® catheter. Areas as low as 50 mm$^2$ may be useful.

The loops 43 experience electromagnetic fields and function as single-axis magnetic sensors. When the loops are subjected to electromagnetic fields at respective frequencies it has been found that the location of each loop can be determined to within 1 mm by combining signals obtained from the loops using the positioning subsystem of the system 10 (FIG. 1). Once the locations of the loops are known, the location of distal end 51 of the catheter can also be determined.

As noted above, the loops 43 are formed of wires. Any conducting material can be used. Suitable materials include copper, stainless steel, and nitinol. Materials having shape memory may be advantageous in maintaining contact between the electrodes 53 and the endocardial surface of the heart chamber. The inventors have found in simulations that the average field strength over a large loop is the same as the field at the centroid of the loop.

The requisite size of the loops relates inversely to the intensity of the magnetic fields produced by field generating coils 28 (FIG. 1). If the field is too weak, then the size of the loops would become impractical as the framework could not be easily accommodated in a cardiac chamber. On the other hand, if the loops were reduced in size, the required magnetic field strength would increase, in which case the field generating coils 28 and generators 25 would become expensive and might require additional protection for the operator and other personnel involved in the procedure. Sensor sensitivity is a function of the total sensor area. It is desirable that the total sensor area be dimensioned such that the sensors operate in magnetic fields generated by the CARTO system and other magnetic localizing systems. For a coil sensor sensitivity is a function of the area per loop times the number of loops. The formula for sensitivity to flux is $$\text{Flux Sensitivity}\left(\frac{\mu V}{Hz\ gauss}\right) = 4\pi 10^{-4}\ \text{Area (mm}^2\text{)}.$$

Electrodes 53 are typically disposed on the loops 43. While only one electrode is shown on each loop in FIG. 2, any number of electrodes may be placed on the loops 43 in order to increase contact between the framework 39 and target tissue, and thereby improve the resolution of the electroanatomic map. The electrodes 53 are linked to the console 24 (FIG. 1) by separate conductors (not shown).

Calibration.

Figure 3:
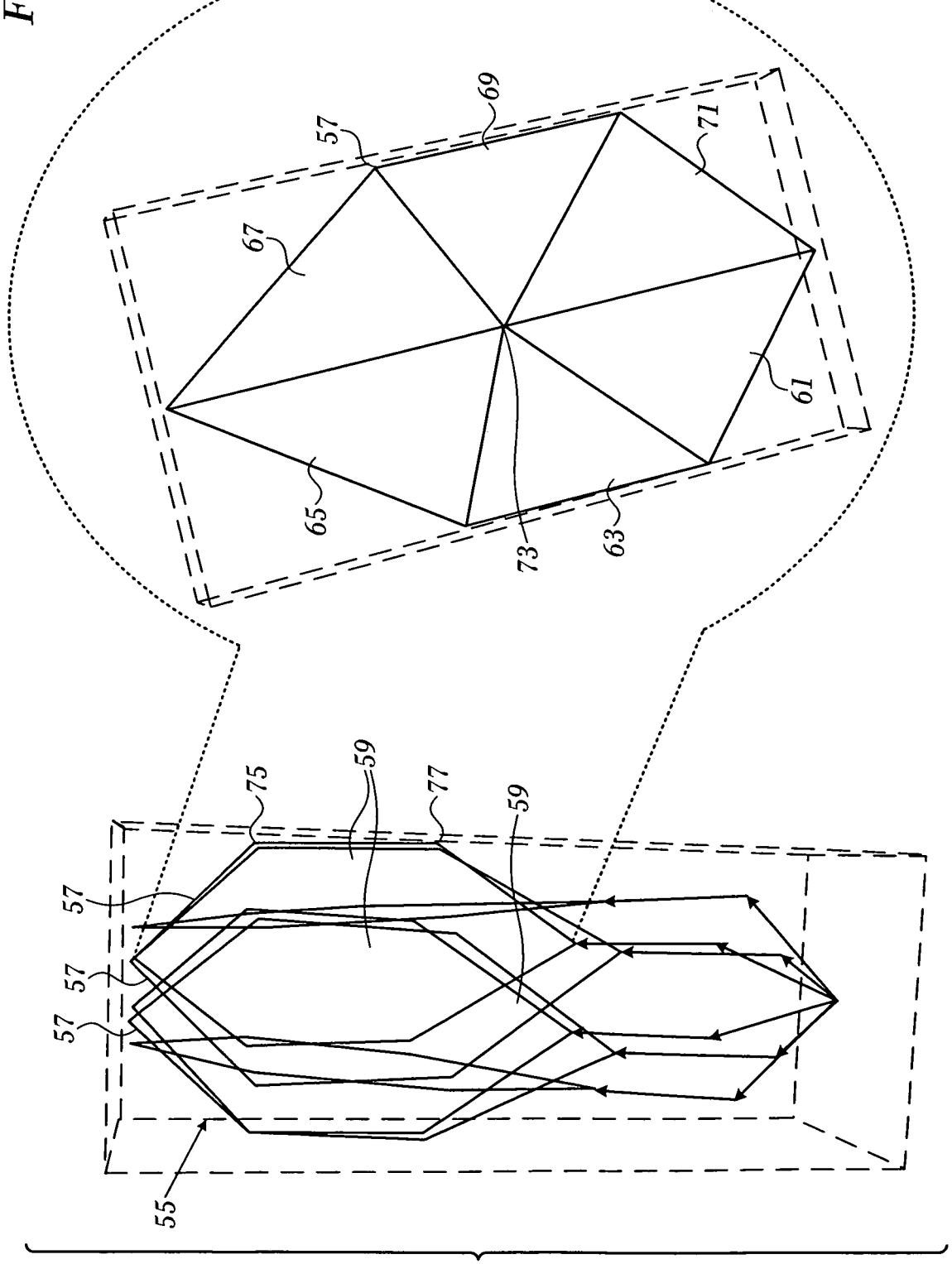
FIG. 3 illustrates a model of a framework in the catheter shown in FIG. 2 in accordance with an embodiment of the invention.

Reference is now made to FIG. 3, which shows a model 55 of the framework 39 (FIG. 2) in accordance with an embodiment of the invention, in which the loops of the framework are here represented as hexagons 57. However, the loops can be approximated by polygons with any number of sides. The polygons need not be regular polygons or even identical, so long as their segments approximately conform to the shapes of the loops. Any such polygon can be partitioned into triangles using an interior point as described below.

The borders of the hexagons 57 define respective surfaces 59. If one of the loops 43 (FIG. 2) lies in a plane, then the integral of the magnetic flux over its surface 59, denoted as A, divided by the area of the loop is equal to the magnetic field at the centroid of the loop. This implies that a large sensor behaves like a small sensor located at the centroid. Using the spherical harmonic expansion model of the CARTO magnetic field, we verified this connection both analytically and numerically.

$$\vec{B}(\text{centroid}) = \frac{\int_{(x,y,z)\in A} \vec{B}(x, y, z)\hat{n}dA}{\text{Area}(A)}. \qquad \text{Eq. (1)}$$

An electrical prototype of several catheters was constructed, where the external structure comprised six hexagonal shaped loops as shown in FIG. 3. The loops were calibrated using calibration procedures as described in U.S. Pat. Nos. 6,370,411 and 6,266,551, both to Osadchy et al., and herein incorporated by reference. The prototype was then tested using a CARTO system with various position shifts controlled by a robot. The resulting locations and orientations matched the relative location of the coil centroids within the catheter structure and the motion of the catheter as performed by the robot.

Simulations.

It is possible to obtain a more detailed representation of the catheter than provided by the set of locations and orientations of the centroids of the loops 43. This is achieved by exploiting knowledge of the structure of the framework 39: specifically the shape of the loops 43 and the nature of intersections between adjacent loops, whether they cross or are tangent.

In one configuration which has been simulated, the loops are modeled as hexagons with various relative dimensions. A useful feature of hexagons is that they can be subdivided into triangles. That means even when the hexagon is deformed, and its border is no longer planar, the theoretical magnetic flux can be modeled as the sum of theoretical magnetic fluxes over the triangular segments, which are, by definition, planar.

FIG. 3 models a catheter whose framework comprises six hexagons 57. As shown at the right of the figure, Each hexagon 57 contains six triangles 61, 63, 65, 67, 69, 71, which have a common vertex 73.

Reference is now made to FIG. 4, which is a representation of the triangles 71 (FIG. 3), in accordance with an embodiment of the invention. The coordinates of each triangle can be defined in its own local coordinate system, $\text{Tri}_{ij}^{local}$, where each $\text{Tr}_i$ is a list of three points. Giving each vertex a label (1, 2, 3), the x-axis is the line connecting points 1 and 2. The origin is the midpoint. The triangle lies in the plane z=0 and point 3 has a positive y-coordinate. We denote the transformations between the local coordinate frames as $R_{ij}^{loc \to CARTO}$ and $T_{ij}^{loc \to CARTO}$ where Rot refers to a 3×3 rotation matrix and T to a translation vector. The index i runs from 1 to 6 and refers to a particular hexagon, and the index j refers to a triangle within the hexagon. In the CARTO coordinate system $\text{Tri}_{ij}^{CARTO} = \text{Rot}_{ij}^{loc \to CARTO} \cdot \text{Tri}_{ij}^{local} + T_{ij}^{loc \to CARTO}$. The theoretical magnetic flux through each can be computed using the relation $$Flux_i = \sum_{j=1}^{6} \int_{(x,y,z) \in Tri_{ij}^{CARTO}} B^{CARTO}(x, y, z) \cdot \hat{n}_{Tri_{ij}^{CARTO}} dA(x, y, z). \qquad \text{Eq. (2)}$$

where dA(x, y, z) represents the surface element over the triangle and $\hat{n}_{Tri_{ij}}^{CARTO}$ is the normal to the triangle, and $B^{CARTO}$ (x, y, z) are the CARTO fields, a set of nine vectors. Each $Flux_i$ is a nine element vector. We can avoid the laborious calculation of surface integrals by applying Equation 1.

Reverting to FIG. 3, the flux through each hexagon 57 is now expressed as $$Flux_i = \sum_{j=1}^{6} \text{Area}(Tri_{ij}^{CARTO}) B^{CARTO}(\text{Centroid}[Tri_{ij}^{CARTO}]) \cdot \hat{n}_{Tri_{ij}^{CARTO}}. \qquad \text{Eq. (3)}$$

The value of the signal from the hexagon is $$Signal_i = \frac{Flux_i}{\sum_{j=1}^{6} \text{Area}(Tri_{ij}^{CARTO})}. \qquad \text{Eq. (4)}$$

Continuing to refer to FIG. 3 and FIG. 4, in order to use the signals in the hexagonal loops of the model 55 to determine the location and orientation of the structure, we have to define the problem differently from tracking of a single sensor. The locations and orientations of the triangles 71 are known in their local coordinate systems. The task is to solve for the parameters of the transformations of each triangle to the CARTO coordinate system. For each triangle 71 there are six unknowns, three rotation parameters and three translation parameters. For each hexagonal loop, each of which contains six triangles, we have one flux measurement from each transmitting coil, nine in the particular case of CARTO. So for a catheter containing n conducting hexagonal loops we have 36×n unknowns to be found using n×9 measured input values. To reduce the effective number of unknown we apply our knowledge of the mechanical structure of the catheter to define constraints on the triangles.

Consider the internal structure of each hexagonal loop. Points 1 of all 6 triangles within a hexagon intersect at the vertex 73.

$$\text{Tri}_{i,j}^{CARTO}(1) = \text{Tri}_{i,k \neq j}^{CARTO}(1) \qquad \text{Eq. (5)}$$

In local coordinates Equation 5 becomes $$\text{Rot}_{i,j}^{loc \to CARTO} \text{Tri}_{i,j}^{local}(1) + T_{i,j}^{loc \to CARTO} = \text{Rot}_{i,k \neq j}^{loc \to CARTO} \text{Tri}_{i,k \neq j}^{local}(1) + T_{i,k \neq j}^{loc \to CARTO} \qquad \text{Eq. (6)}$$

Another set of constraints on the internal structure is that point 3 of each triangle coincides with point 2 of the adjacent triangle.

$$\text{Tri}_{i,\{1,2,3,4,5,6\}}^{CARTO}(3) = \text{Tri}_{i,\{2,3,4,5,6,1\}}^{CARTO}(2) \qquad \text{Eq. (7)}$$

We can also define constraints based on the relative disposition of the hexagonal loops. In the present configuration adjacent frames touch each other at two points, best seen in FIG. 3 as points 75, 77. Each vertex of the hexagons 57 is labeled with two indices. The first indexes each of the triangles 61, 63, 65, 67, 69, 71. The second indexes the vertices (1, 2, 3) within each triangle of the hexagons.

Reference is now made to FIG. 5, which is a diagram similar to FIG. 3 that illustrates the intersection of faces of model 55 in accordance with an embodiment of the invention: Indices of the hexagons and triangles are shown. Consider the intersections in visible in the front of the diagram. Segment 79 (defined by points (3,2), (3,3)) of hexagon 81 on the right intersects segment 83 (defined by points (2,2), (2,3)) of hexagon 82. In like manner, segment 86 (defined by points (5.2), (5,3)) of hexagon 81 intersects segment 84 (defined by points (6,2),(6,3)) of hexagon 82.

A fit was performed that included the following conditions:

A vertex of each triangle meets at the center of a hexagon;
The other vertices of the triangles meet at points defining the vertices of a hexagon;
The measured flux from each hexagon equals the sum of the estimated fluxes through each triangle; and
There are wire crossing constraints, i.e., the triangles intersect at points, e.g., the intersections of segments 79, 83 and segments 84, 86.

There is more than one way to define this constraint. Distances between two skewed lines may be computed using the formula $$D = \frac{|(x_3 - x_1) \cdot [(x_2 - x_1) \times (x_4 - x_3)]|}{|(x_2 - x_1) \times (x_4 - x_3)|},$$

where the differences are all vectors. The vectors $x_1$ and $x_2$ are endpoints of one segment, and the vectors $x_3$ and $x_4$ are endpoints of the other. This involves the addition of no[1] new parameters. For computational reasons we found it more convenient to define two parameters, $v_{12}$ and $v_{34}$, the distance along the segments, and define the constraint as follows $$x_1 + v_{12}(x_2 - x_1) = x_3 + v_{34}(x_4 - x_3) \qquad \text{Eq. (8)}.$$

For calculation purposes each of the terms $x_i$ is expressed in terms of the local triangles and the transformations to the CARTO coordinate system.

Given a set of measurements for an array of hexagons defined by vertices or points, either from experiment or simulations, The parameters are found by optimizing a first cost function, wherein.

$meas_i$ is the $i^{th}$ measured signal from the system; and
$locMeas_i$ is the location of the $i^{th}$ point.

The value $locMeas_i$ is determined, mutatis mutandis, by the method, disclosed in detail in commonly assigned U.S. Pat. No. 8,818,486, which is herein incorporated by reference. Briefly, the method involves generating a magnetic field in a predefined volume. A reference model is defined, which models the magnetic field at multiple points in the volume using spherical harmonics. The magnetic field is measured by a field detector, which is coupled to an intrabody probe inserted into an organ of a living body located in the volume. A second cost function is defined by comparing the measured magnetic field with the reference magnetic field model within the volume. The cost function is minimized by a computation over dipole terms in a derivative over the cost function so as to find a position and orientation that matches the measured magnetic field. The found position and orientation is outputted as the position and orientation of a probe in the organ.

The following constraints are incorporated into the cost function: Centroid constraint, $$cost_{centroid} = \sum_{i=1}^{6} (locMeas_i - Tri_{i1}^{CARTO}(1))^2$$

The location of the first point in triangle 1 of each hexagon matches the location found by using the measured signal from the hexagon.

Flux Sum Constraint:

The term $B^{CARTO}(x,y,z)$ is the estimated field value at a location using a mathematical model such as described in the above-noted U.S. Pat. No. 8,818,486. That implies that the value $Signal_i$ is also a model based value.

$$cost_{Flux\_Hex} = \sum_{i=1}^{6} (meas_i - Signal_i)^2.$$

Optimally, the estimated flux in each hexagon matches the measured flux.

Triangle Points 1 for each hexagon meet:

$$cost_{vertex1} = \sum_{i=1}^{6(hexagons)} \sum_{j=2}^{6(triangles)} \|(Tri_{i1}^{CARTO}(1) - Tri_{ij}^{CARTO}(1))\|^2$$

Point 3 of each triangle in a hexagon meets point 2 of the next triangle:

$$cost_{triangles} = \sum_{i=1}^{6} \begin{pmatrix} \|Tri_{i1}^{CARTO}(3) - Tri_{i2}^{CARTO}(2)\|^2 + \|Tri_{i2}^{CARTO}(3) - Tri_{i3}^{CARTO}(2)\|^2 + \\ \|Tri_{i3}^{CARTO}(3) - Tri_{i4}^{CARTO}(2)\|^2 + \|Tri_{i4}^{CARTO}(3) - Tri_{i5}^{CARTO}(2)\|^2 + \\ \|Tri_{i5}^{CARTO}(3) - Tri_{i6}^{CARTO}(2)\|^2 + \|Tri_{i6}^{CARTO}(3) - Tri_{i1}^{CARTO}(2)\|^2 \end{pmatrix}$$

Adjacent hexagons meet at a point. The following equations show the meeting of triangle 3 from one hexagon with triangle 4 of the adjacent hexagon, e.g., segments 79, 83.

$$x1_i = Tri_{i4}^{CARTO}(2)$$

$$x2_i = Tri_{i4}^{CARTO}(3)$$

If $i < 6$ $$x3_i = Tri_{1,3}^{CARTO}(2)$$

$$x4_i = Tri_{1,3}^{CARTO}(3)$$

$$x3_6 = Tri_{1,3}^{CARTO}(2)$$

$$x4_6 = Tri_{1,3}^{CARTO}(3)$$

$$cost_{cross\_top} = \frac{((x3_i - x1_i) \cdot ((x2_i - x1_i) \times (x4_i - x3_i)))^2}{\|((x2_i - x1_i) \times (x4_i - x3_i))\|^2}$$

The following equations show the meeting of triangle 6 from one hexagon with triangle 1 of adjacent hexagon, e.g., segments 84, 86 (84 and 85 of FIG. 5)

$$x1_i = Tri_{i6}^{CARTO}(2)$$

$$x2_i = Tri_{i6}^{CARTO}(3)$$

If $i < 6$ $$x3_i = Tri_{1,1}^{CARTO}(2)$$

$$x4_i = Tri_{1,1}^{CARTO}(3)$$

$$x3_6 = Tri_{1,1}^{CARTO}(2)$$

$$x4_6 = Tri_{1,1}^{CARTO}(3)$$

$$cost_{cross\_bottom} = \frac{((x3_i - x1_i) \cdot ((x2_i - x1_i) \times (x4_i - x3_i)))^2}{\|((x2_i - x1_i) \times (x4_i - x3_i))\|^2}$$

The total cost function to be minimized is $$cost_{full} = w1\ cost_{centroid} + w2\ cost_{Flux\_Hex} + w3\ cost_{vertex1} + w4\ cost_{triangles} + w5\ cost_{cross\_top} + w6\ cost_{cross\_bottom}$$

The variables w1-w6 are relative weighting terms. In the results presented here they are all set to 1.

The parameters are found by minimizing the above cost function. In simulations, the optimization is begun with the entire structure displaced and deformed by bending at some of the hexagon joints. The reconstruction accuracy was at the sub-millimeter level.

Figure 6:
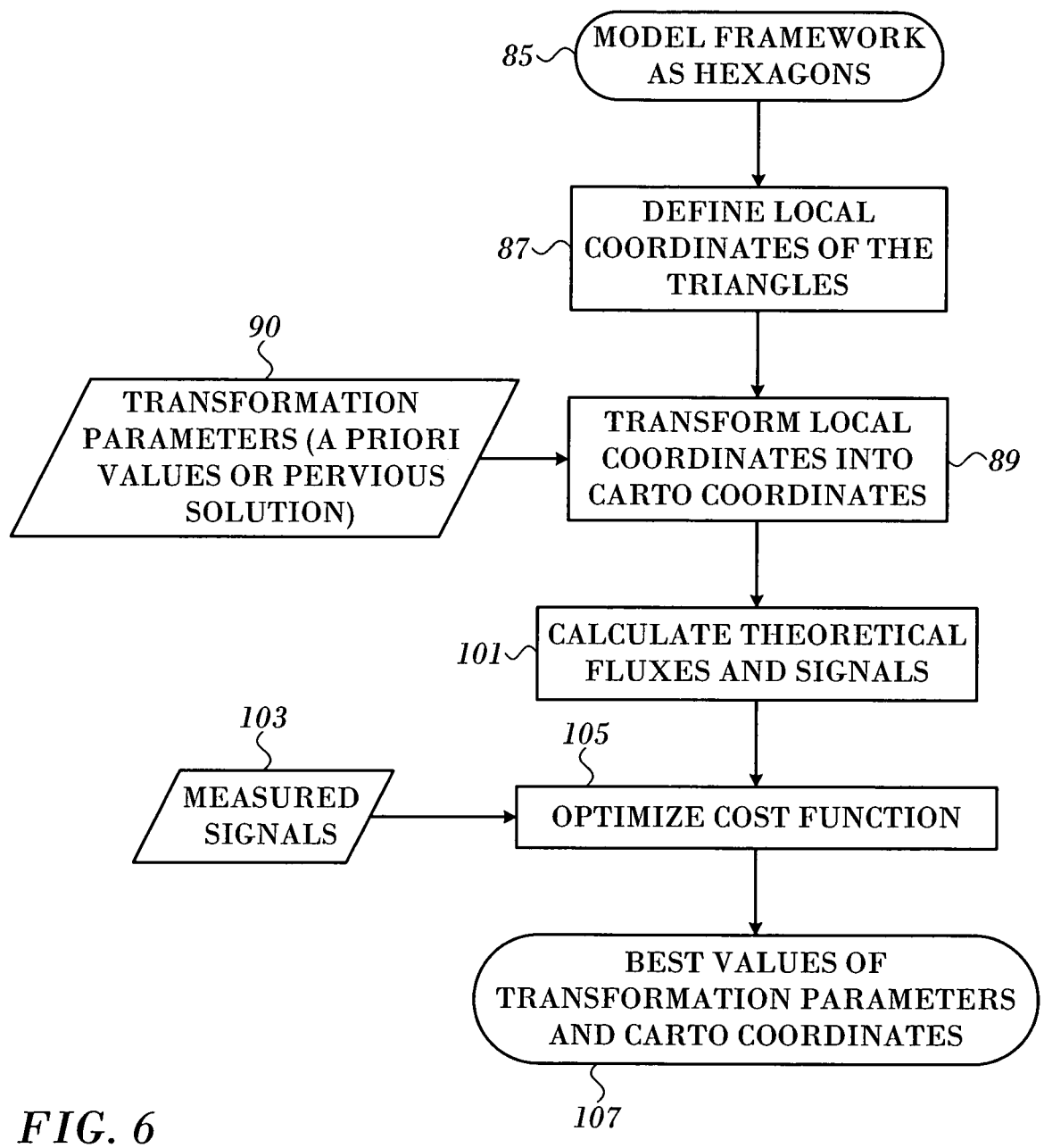
FIG. 6 is a flow chart of a procedure for determining a catheter frame location in accordance with an embodiment of the invention.

Reference is now made to FIG. 6, which is a flow chart summarizing the procedure for determining the catheter location in accordance with an embodiment of the invention.

At initial step 85 a catheter framework is modeled as a series of hexagons subdivided into triangles.

Next, at step 87 local coordinates of each triangle are defined.

Next, at step 89 the local coordinates of the triangles are transformed into CARTO coordinates. The initial parameters of the transform can be a priori values or can be obtained from a previous solution as shown in step 90.

Next, at step 101 theoretical fluxes and signals for the triangles and hexagons are obtained as described above.

Step 103 applies measured signals to the solution in step 103 for the parameters of the transformations of each triangle to the CARTO coordinate system by optimizing the cost function described above—applying Equation 4 and Equation 5 to the triangles using their areas and centroids (in CARTO coordinates) to compute the flux in each of the hexagons and then to compute the signal obtained from each of the hexagons.

At final step 107 the location of the catheter is reported, using the best values of the transformation parameters and Carto coordinates.

Example

A fit was performed that included the following conditions:
- a vertex of each triangle meets at the center of a hexagon;
- the other vertices of the triangles meet at points defining the vertices of a hexagon;
- the measured flux from each hexagon equals the sum of the estimated fluxes through each triangle;
- the hexagons are not deformed; and
- the wire crossing constraint is met using the formula.

$$D = \frac{|(x_3 - x_1) \cdot [(x_2 - x_1) \times (x_4 - x_3)]|}{|(x_2 - x_1) \times (x_4 - x_3)|}.$$

Figure 7:
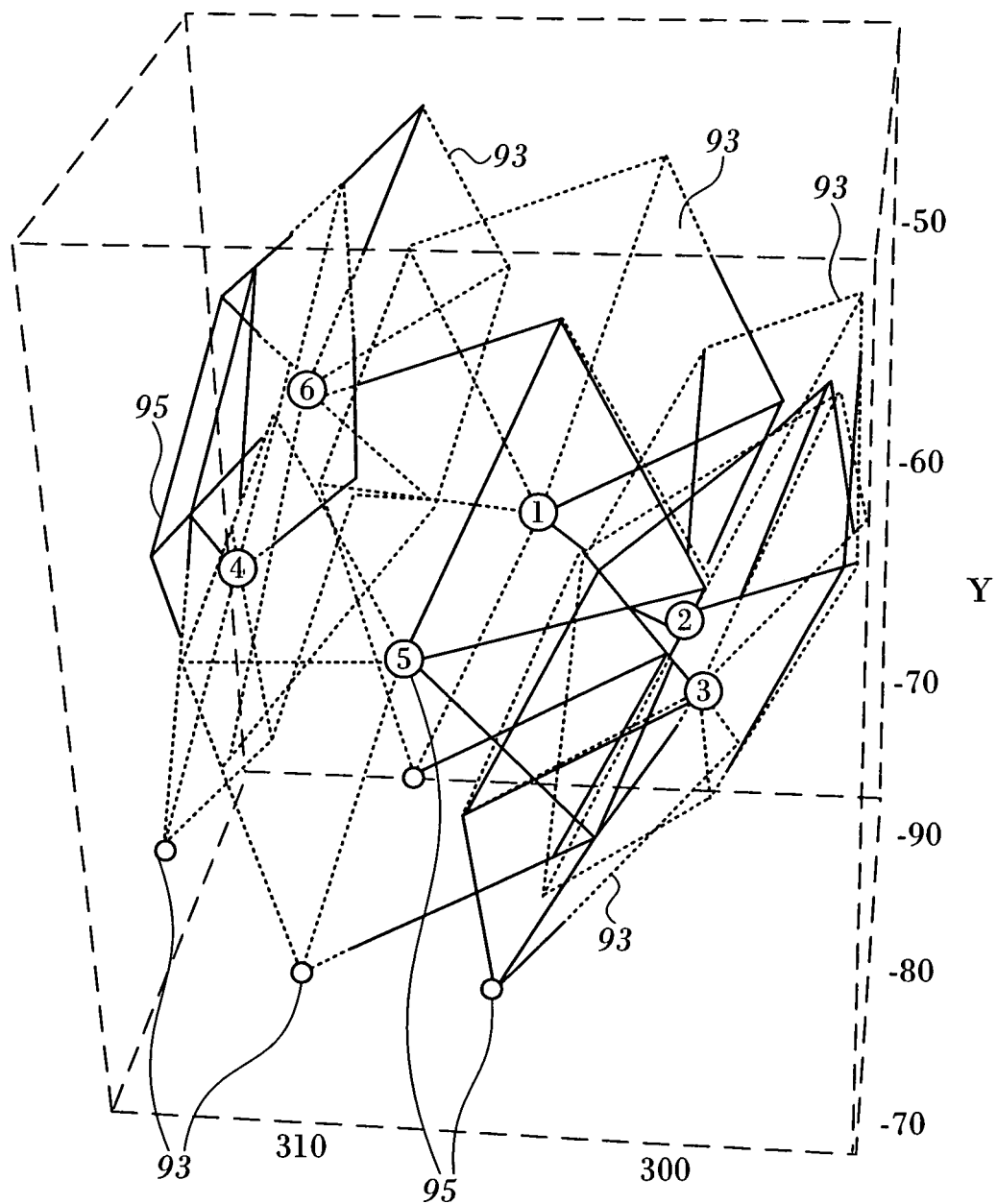
FIG. 7 is a reconstruction of a catheter framework in accordance with an embodiment of the invention.
Figure 8:
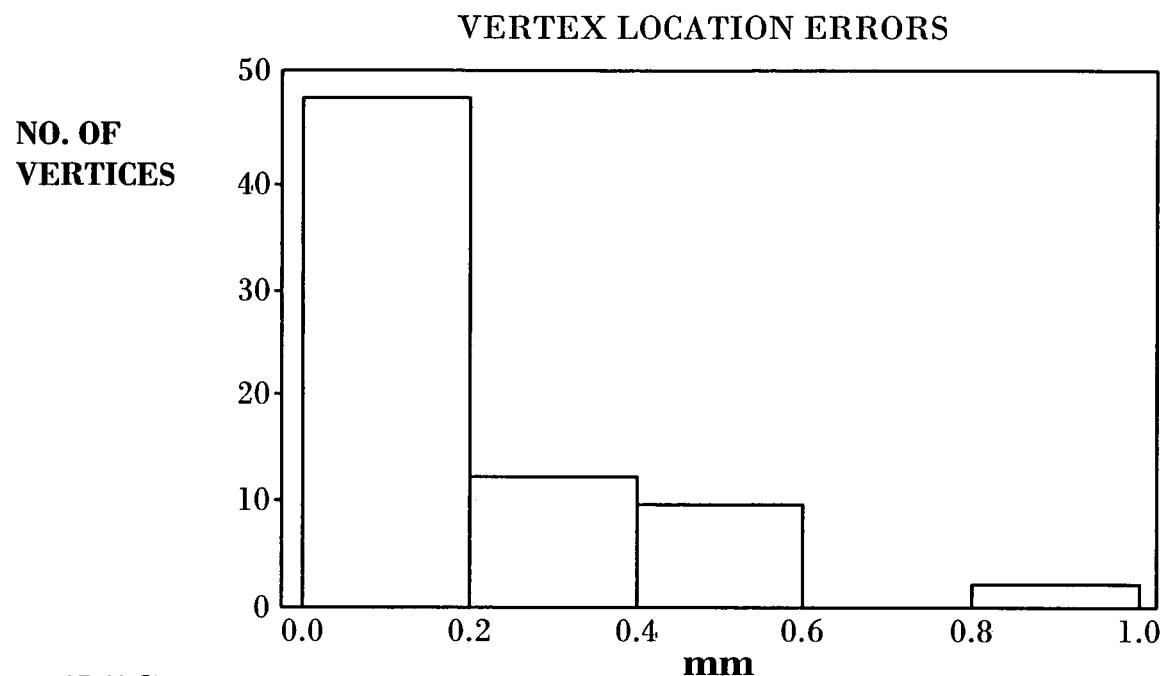
FIG. 8, which is a bar chart describing an aspect of the reconstruction of FIG. 7.

Reference is now made to FIG. 7, which is an exemplary reconstruction of a catheter framework similar to the framework 39 (FIG. 2) using data obtained using a robot, in accordance with an embodiment of the invention and complying with the above-noted conditions. The figure shows an exemplary robot position. The procedure described with respect to FIG. 6 may be used to compute the signals obtained from hexagons 93. More generally, the procedure of FIG. 6 is applicable to models of frameworks containing any number of loops. Reconstructed hexagons 93 are shown in solid lines and hexagons 95 in broken lines. The hexagons 95 represent actual positions of the loops based on knowledge of the robot location and engineered geometry of the catheter Reference is now made to FIG. 8, which is a bar chart showing the result of the fit. The chart shows the distribution of errors in the locations of each point on the triangles. This result is for one of 27 robot locations. The other locations give similar results.

Figure 9:
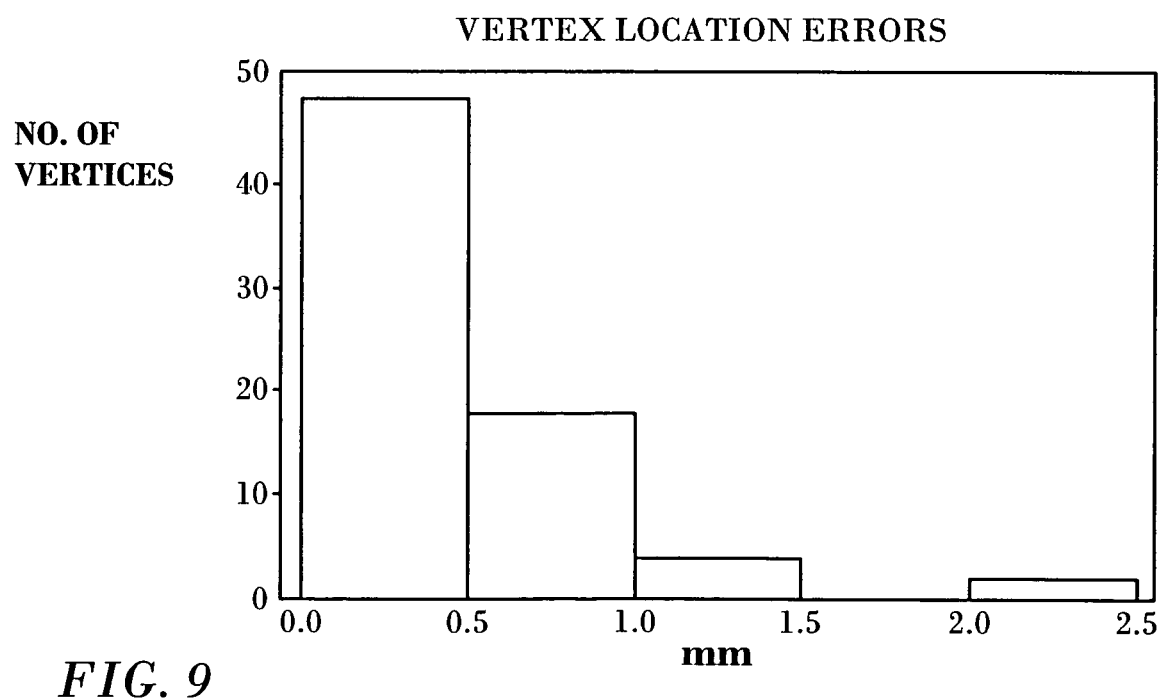
FIG. 9 is a bar chart describing a simulated reconstruction in accordance with an embodiment of the invention.

When the hexagons are allowed to deform by bending at the vertices, which is the case in an actual flexible catheter, simulations show a slight loss of accuracy. Reference is now made to FIG. 9, which illustrates a simulated fit in which the hexagons were allowed to deform in accordance with an embodiment of the invention. The vertex location errors tend to be larger than those shown in FIG. 8.

Alternate Embodiment

Figure 10:
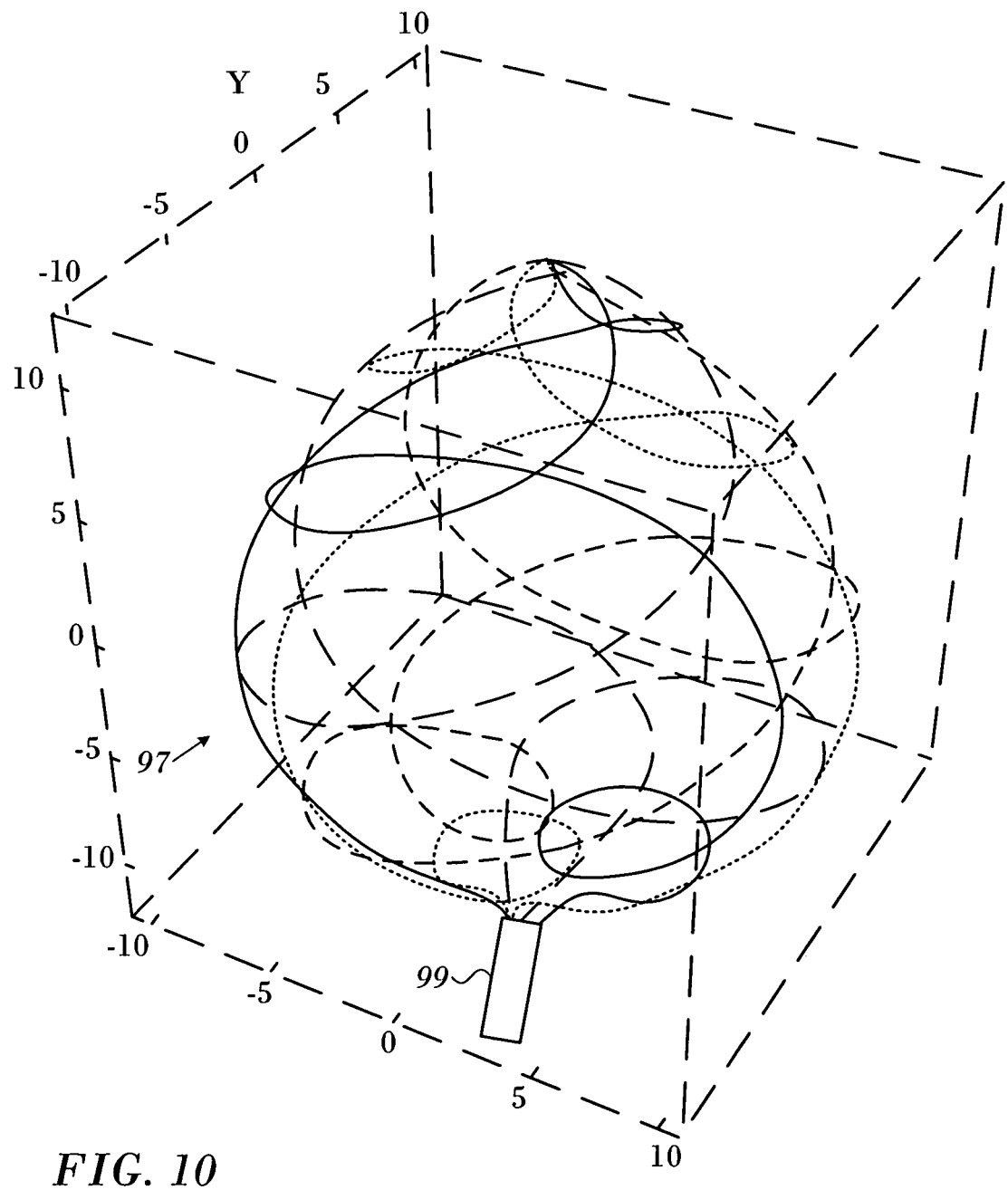
FIG. 10 shows a wire framework in accordance with an alternate embodiment of the invention.

The construction of a wire framework is not limited to the embodiment shown in FIG. 2. The principles of the invention can be applied to other frame shapes and arrangement. Reference is now made to FIG. 10, which shows a wire framework 97 deployable through a catheter 99, in accordance with an alternate embodiment of the invention. Individual wires spiral about an axis, contact one another and form closed loops as in FIG. 2. The pitch of the spirals may be identical, but are not necessarily so. Other constructions will occur to those skilled in the art and may be applied as described above.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising:
   inserting a probe into an organ of a living subject, the probe having a distal end having a framework disposed on the distal end, the framework comprising a plurality of electrically conducting wire loops defining a chamber, each of the loops functioning independently as a single-axis magnetic location sensor when subjected to the magnetic field produced by field generating coils, the loops being connected to a magnetic tracking system having a field generating coils disposed around the living subject;
   modeling the wire loops as respective polygons;
   subdividing the polygons into a plurality of triangles,
   identifying local coordinates of the triangles in a local coordinate system; and
   transforming the local coordinates of the triangles to coordinates of the magnetic position tracking system;
   exposing the wire loops to magnetic fluxes at respective frequencies provided by the field generating coils;
   reading signals from the wire loops responsively to the magnetic fluxes at the respective frequencies;
   computing the theoretical magnetic fluxes in the polygons as respective sums of theoretical magnetic fluxes in the triangles thereof; and
   determining a location and orientation of the framework by relating the computed theoretical magnetic fluxes to the signals and reporting a position and orientation of the probe in the organ.

2. The method according to claim 1, wherein the polygons comprises hexagons.

3. The method according to claim 2, wherein transforming the local coordinates is performed by optimizing a cost function.

4. The method according to claim 1, wherein computing the theoretical magnetic fluxes is based on areas and centroids of the triangles.

5. The method according to claim 1, wherein modeling the wire loops further comprises applying a first constraint, wherein segments of the triangles of adjacent polygons are required to intersect.

6. The method according to claim 1, wherein modeling the wire loops further comprises applying a second constraint, wherein a vertex of each triangle of one polygon coincides with a vertex of an adjacent triangle of the one polygon.

7. The method according to claim 1, wherein modeling the wire loops further comprises applying a third constraint, wherein adjacent polygons contact one another at exactly two points.

8. The method according to claim 1, wherein the loops comprise three to eight loops.

9. The method according to claim 1, wherein the loops comprise six to seven loops.

10. The method according to claim 1, wherein the loops form spirals about an axis.

11. The method according to claim 1, wherein the wire loops are deformable, further comprising deploying the framework through a lumen of the probe.

12. The method according to claim 1, wherein one of the loops contacts at least another one of the loops.

* * * * *